United States Patent [19]

Liu et al.

[11] 4,137,241
[45] Jan. 30, 1979

[54] DEOXY-(O-8)-EPI-17-SALINOMYCIN (1)

[75] Inventors: Chao-Min Liu; John Westley, both of Cedar Grove, N.J.

[73] Assignee: Hoffmann-La Roche Inc., Nutley, N.J.

[21] Appl. No.: 785,482

[22] Filed: Apr. 7, 1977

[51] Int. Cl.$^2$ .......................................... C07D 309/22
[52] U.S. Cl. .............................. 260/345.7 R; 424/283
[58] Field of Search ................. 260/345.7 R, 345.8 R

[56] References Cited
U.S. PATENT DOCUMENTS 3,857,948  12/1974  Tanaka et al. ...................... 424/283

FOREIGN PATENT DOCUMENTS 51-86191  7/1976  Japan ..................................... 260/345.9

*Primary Examiner*—Nicky Chan
*Attorney, Agent, or Firm*—Jon S. Saxe; Bernard S. Leon; Frank P. Hoffman

[57] ABSTRACT

A compound which is the C-17 epimer of deoxy-(0-8)-epi-17-salinomycin is produced by the fermentation of a strain of *Streptomyces albus* 80,614 (ATCC 21,838). The compound exhibits activity as an antimicrobial and antihypertensive agent.

1 Claim, No Drawings

DEOXY-(0-8)-EPI-17-SALINOMYCIN (1)

DESCRIPTION OF THE INVENTION

A novel antimicrobial compound is provided in a pure form, designated as the C-17 epimer of deoxy-(0-8)-salinomycin (deoxy-(0-8)-epi-17-salinomycin) produced by the fermentation of a strain of *Streptomyces albus* 80,614 on deposit at the American Type Culture Collection, Rockville, Md. having the accession number 21,838. The same microorganism is utilized in the production of salinomycin (II). Morphological characteristics of the microorganism are disclosed in U.S. Pat. No. 3,857,948 issued December 31, 1974 to Tanaka et al., the teaching of which is incorporated herein by reference.

The compound in its pure form exhibits activity as an antimicrobial agent and as an antihypertensive agent.

The novel compound of the present invention has the following structure (I) in comparison to the known compound salinomycin (II) also depicted below.

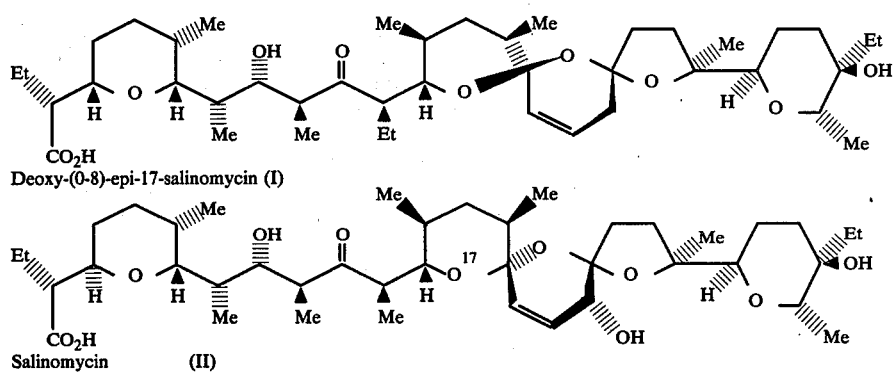

Deoxy-(0-8)-epi-17-salinomycin (I)

Salinomycin (II)

The novel compound of the present invention has the chemical name 6-[5-[2'-(5''-Ethyltetrahydro-5''-hydroxy-6''-methyl-(2''H)-pyran-2''-yl]-2',12',14'-trimethyl-1',10',15'-trioxadispiro[4.3.5.1]pentadec-7'-en-11'-yl]-5-ethyl-1,3-dimethyl-2-hydroxy-4-oxopentyl]-alpha-ethyl-tetrahydro-5-methyl-(2H)-pyran-2-acetic acid.

The compound is produced by the fermentation of a strain of *Streptomyces albus* 80,614 (ATCC 21,838). A fermentation broth containing *Streptomyces albus* 80,614 is prepared by inoculating spores or mycelia of the compound producing organism into a suitable medium and then cultivating under aerobic conditions. For the production of the epimeric compound cultivation on a solid medium is possible but for production in large quantities cultivation in a liquid medium is preferable. The temperature of the cultivation may be varied over a wide range, 20°-35° C, within which the organism may grow but a temperature of 26°-30° C and a substantially neutral pH is preferred. In the submerged aerobic fermentation of the organism for the production of the compound, the medium may contain as the source for carbon, a commercially available glyceride oil or a carbohydrate such as glycerol, glucose, maltose, lactose, dextrin, starch, etc. in pure or crude states and as the source of nitrogen, an organic material such as soybean meal, distillers solubles, peanut meal, cotton seed meal, meat extract, peptone, fish meal, yeast extract, corn steep liquor, etc. and when desired inorganic sources of nitrogen such as nitrates and ammonium salts and mineral salts such as ammonium sulfate, magnesium sulfate and the like. It also may contain sodium chloride, potassium chloride, potassium phosphate and the like and buffering agents such as sodium citrate, calcium carbonate or phosphates and trace amounts of heavy metal salts. In aerated submerged culturing procedures, an anti-foam agent such as liquid paraffin, fatty oils or silicone compounds is used. More than one kind of carbon source, nitrogen source or anti-foam source may be used for production of the epimeric compound. Generally the cultivation is continued until at least several hundred mcg/ml of compound has accumulated in the medium.

Considered within the ambit of the present invention are the organic or inorganic pharmaceutically acceptable salts of deoxy-(0-8)-epi-17-salinomycin. These salts are prepared from the free acid by methods well known in the art, for example, by washing the free acid in solution with a suitable base or salt. Examples of such pharmaceutically acceptable basic substances capable of forming salts for the purpose of the present invention include alkali metal bases such as sodium hydroxide, potassium hydroxide, lithium hydroxide and the like alkaline earth metal bases, such as calcium hydroxide, barium hydroxide and the like; and ammonium hydroxide. Alkali metal or alkaline earth metal salts suitable for forming pharmaceutically acceptable salts can include anions such as carbonate, bicarbonate and sulfates. Preferred for use in this invention are salts formed from alkali metal bases.

Examples of organic bases forming pharmaceutically acceptable salts with the deoxy-(0-8)-epi-17-salinomycin are lower alkyl amines, primary, secondary and tertiary hydroxy-lower alkylamines such as ethylamine, isopropylamine, diethylamine, methyl-n-butylamine, ethanolamine and diethanolamine.

The following examples serve to illustrate this invention without limiting it thereto.

EXAMPLE 1

Inoculum Preparation

Shaker flask "seed" inoculum is prepared by inoculating a 100 ml. portion of sterile liquid medium in a 500 μl flask with scrapings or washings of spores from an agar slant of the culture. The following medium is ordinarily used.

Cerelose 20 grams
Starch 10 grams
Soybean meal 25 grams
Debittered yeast 2 grams
Dried meat extract 1 gram NaCl 2 grams
Water to 1000 ml
pH to 7.0 before autoclaving The flasks are incubated at a temperature from 25–29° C., preferably 28° C., and agitated on a rotary shaker at 250 rpm for 72 hours. From this 100 ml portion of seed inoculum two 10 ml to 15 ml portions are used to inoculate two 2 liter batches of the same medium in 6 liter flasks. The inoculum mash is agitated on a rotary shaker at 250 rpm for 72 hours at which time they are in turn used to inoculate the tank fermentor.

EXAMPLE 2

Tank Fermentation

For the production of these antibiotics in tank fermentors the following fermentation medium is preferably used.

Cerelose; 10 grams
Edible Molasses (black strap); 20 grams
Hy Soy T; 5 grams
$CaCO_3$; 2 grams
SAG 4130 (Union Carbide); 0.1 grams
Water to; 1000 milliliters
pH to 7.2 before autoclaving The 60 gallon tank is inoculated with the two inoculum flasks (1.7%) described above. Aeration is supplied at the rate of 3 cubic foot of sterile air per 60 gallon of broth per minute and the fermenting mixture is agitated by an impeller driven at 200–400 rpm, usually 280 rpm. The temperature is maintained at 25–29° C., usually 28° C. The fermentation is ordinarily continued for 144 hours at which time the mash is harvested.

EXAMPLE 3

Isolation of deoxy-0-8)-epi-17-salinomycin

The 36 gallons of whole broth from a 142 hour fermentation of S. albus 80,614 was extracted once with an equal volume of ethyl acetate at the harvest pH. The solvent layer was separated and concentrated under reduced pressure to an oil. The oil dissolved in 1 liter of $CH_3CN$ and washed with 1 liter of $n-C_6H_{14}$. The $CH_3CN$ was concentrated under reduced pressure to 150 ml, filtered, and washed an additional 6 times with a total of 1 liter $n-C_6H_{14}$. From the $CH_3CN$ layer after concentration and addition of $H_2O$ the end product was recovered by filtration. From the pool of $n-C_6H_{14}$ washes additional end product was recovered by $CH_3OH$ extraction and crystal.

In view of the antimicrobial activity of the C-17 epimer of dexoy-(0-8)-salinomycin as set forth in Table I below, a utility for the antimicrobial compound would be as a disinfectant in wash solutions for sanitary purposes as in the washing of bands and the cleaning of equipment, floors or furnishings of contaminated rooms or laboratories. It is also useful for suppressing the growth of sensitive organisms in plate assays and other microbiological media.

The novel compound of the present invention exhibited the following in vitro activities against various organisms.

TABLE I

| Antimicrobial Spectrum Test Organism | M.I.C. Values in mcg/ml utilizing the agar diffusion technique |
|---|---|
| Sarcina lutea | 25 |
| Bacillus megaterium | 6.25 |
| Bacillus subtilis | 6.25 |
| Staphylococcus aureus | 25 |
| Bacillus sp. TA | 6.25 |
| Mycobacterium phlei | 500 |
| Actinomyces cellulosae | 250 |
| Paecilomyces varioti | 15.7 |
| Candida albicans | 2000. |
| Bacillus sp. E | 6.25 |

A test was conducted for antihypertensive activity in the DOCA Na rat. DOCA rats weighing 170 to 210 grams are used in the test. DOCA Na Hypertension is induced by unilateral nephrectomy followed by subcutaneous implantation of a 25 mg. desoxycorticosterone (DOCA) pellet. Animals are placed in individual cages receiving 0.9% sodium chloride solution to drink and rat chow diet ad libitum. Two weeks are allowed to elapse from the time of surgery for development of hypertension, i.e., systolic blood pressure of at least 150 mmHg.

Systolic blood pressure and heart rate are measured indirectly from the tail pressure pulse of unanesthetized rats, using a pneumatic pulse transducer. Control readings are taken prior to drug and post drug readings are taken at 1, 3, 6 and 24 hours.

The experimental results are represented as absolute values. Drug-related alterations in systolic blood pressure are expressed as percentage change by comparing control absolute values with post drug absolute values. Compounds are considered active when about a 15% or greater reduction in blood pressure is obtained. However, the reduction in blood pressure must show mathematical significance ($p<0.5$).

A derivative of the polyether ionophore, lasalocid, i.e., the bromo derivative of lasalocid, was tested in the above screen. The compound was orally administered for a five-day period by intubation and thereafter dosing was discontinued but blood pressure monitoring was continued. The following table illustrates the results obtained utilizing bromolasalocid as the test drug.

TABLE 2

| Oral Dose mg/kg Per Day For 5 Days | No. of Rats in Group | Average Systolic Blood Pressure (mm11g) Per Group | | | | | | | | | |
|---|---|---|---|---|---|---|---|---|---|---|---|
| | | Day 1 | | Day 2 | | Day 3 | | Day 4 | | Day 5 | |
| | | am | pm | am | pm | am | pm | am | pm | am | pm |
| 5 | 6 | 209 | 193 | 206 | 194 | 204 | 191 | 206 | 201 | 197 | 196 |
| 10 | 12 | 217 | 192* | 181* | 166* | 171* | 163* | 173* | 157* | 176* | 166* |

*p < .05
The Day 1 a.m. blood pressure readings are the pre-drug controls.
Blood pressure remained below control for a ten (10) day period after drug dosing for the first five consecutive days.

Using bromolasalocid as a standard for comparison, a number of the novel episalinomycin of the present invention was tested for antihypertensive activity. The tests were conducted utilizing single oral dosages in the DOCA-Na. rat over a five-day period with dosing discontinued thereafter. Blood pressure monitoring was carried out for the five-day period and daily after cessation of dosing until blood pressure returned to predrug levels. The daily dosage was calculated by using oneone hundredth (1/100) of the oral (per os) toxicity (LD$_{50}$) up to a maximum of 10 mg/kg/day. The antihypertensive activity expressed as AHR (Subacute antihypertensive ratio) was calculated using bromolasalocid as the standard reference (Table III). From these results, it is apparent that differences exist in onset and duration of antihypertensive activity and potency but that the tested compound exhibited antihypertensive activity.

Table 3

| Name | M61K6 LD$_{50}$ | AHR* | Onset to Max. Response (Day) | Duration of Effect (Days) |
|---|---|---|---|---|
| Bromolasalocid | 1200 | 1.0 | 4 | 15 |
| Deoxy-(0-8)-epi-17-Salinomycin | >1000 | 0.26 | 3 | 4 |

*AHR (Subacute antihypertensive ratio) = $\frac{\text{Antihypertensive Response/Dose (test compound)}}{\text{Antihypertensive Response/Dose (Bromo-lasalocid)}}$ Analytically the free acid of the novel compound of the present invention exhibits the following physical characteristics:

m.p. 180° C, [α]D-59° (cl, CHCl$_3$); vmax (KBr) 970, 1030, 115(C-O-C), 1710 (CO$_2$H), 3420, 3530 cm$^{-1}$(OH); from (EtOH) 280 mm (74); n.m.r.(CDCl$_3$) at 5.4 (H,d of d, cis CH=CH, J=10.5Hz) and 5.85 (H,m) cis CH-CHO. Mass spectrometry of (I) gave a molecular ion at m/e 734 consistent with a formula of C$_{42}$H$_{70}$O$_{10}$. Other major peaks at m/e 716 and 698 are the result of dehydrations and a small peak at m/e 591 probably arises from loss of the A ring. The base peak at m/e 474-(IIIa, see Scheme) is the most useful in distinguishing (I) from salinomycin (II) which has a molecular formula C$_{42}$H$_{70}$O$_{11}$.

Analysis (I) Calcd. C 68.63 H 9.60 O.
Found C 68.34 H 9.33 O.

teral, may be possible. The oral dosage forms include tablets, capsules, dragees, suspensions, solutions and the like. The identify of the inert adjuvant materials which are used in formulating the active ingredient into oral dosage forms will be immediately apparent to persons skilled in the art. These adjuvant materials, either inorganic or organic in nature, include, for example, gelatin, albumin, lactose, starch, magnesium stearate, preservatives (stabilizers), melting agents, emulsifying agents, salts for altering osmotic pressure, buffers, etc., which can be incorporated, if desired, into such formulations.

It has been found that subacute oral administration of the active ingredient, i.e., dosing up to five (5) days with discontinuance thereafter, in a warm-blooded animal, e.g., the DOCA Na. hypertensive rate, is most effective when the dose level is within the range of about 5 mg/kg/day to about 100 mg/kg/day, more preferably about 5/mg/kg/day to about 10 mg/kg/day. Chronic oral administration of the active ingredient, i.e., dosing over five (5) days, is most effective when a low dose level is utilized, i.e., less than 0.1 mg/kg/day, e.g., 0.01 mg/kg/day to about 5 mg/kg/day. The above dosage regimens may also be utilized when treating other cardiovascular problems as alluded to previously, i.e., in reverting the hemodynamic profile to a normal state.

Of the above dosage regimens, most preferred is the chronic low level administration of the active ingredient, i.e., less than 0.1 mg/kg/day to about 1 mg/kg/day. The dosage administered to a particular individual should be varied within the above dosage range, based on the desired antihypertensive effect as a function of the weight and physical condition of the individual patient. Therefore, an effective dosage amount of active compound can only be determined by the clinician

SCHEME

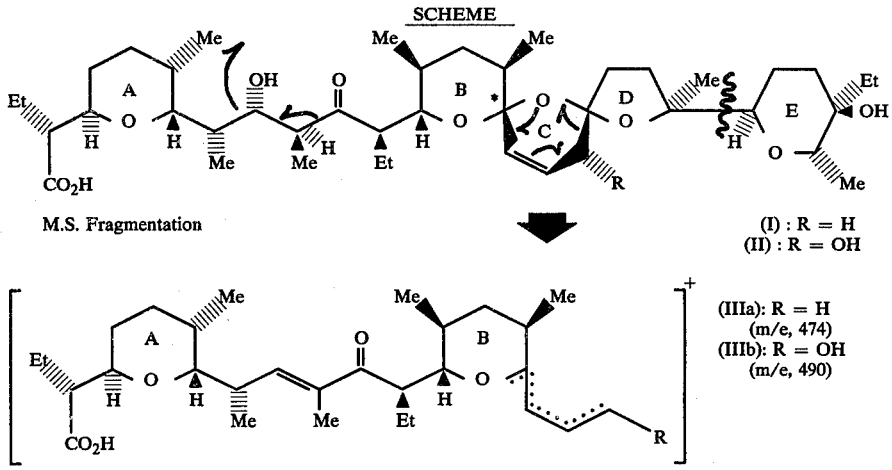

M.S. Fragmentation (I) : R = H
(II) : R = OH (IIIa): R = H (m/e, 474)
(IIIb): R = OH (m/e, 490)

The structure of the compound was determined by X-ray analysis.

For use as antihypertensive agents, the active agent is formulated, using conventional inert pharmaceutical adjuvant materials, into dosage forms which are suitable for oral administration. Other dosage forms, e.g., parenteral utilizing his best judgment on the patient's behalf.

What is claimed is:
1. The compound:
deoxy-(0-8)-epi-17-salinomycin.

* * * * *